United States Patent
Gil et al.

(10) Patent No.: US 9,709,532 B2
(45) Date of Patent: Jul. 18, 2017

(54) PIPELINE INSPECTION DEVICE AND PIPELINE INSPECTION SYSTEM

(71) Applicants: KOREA ELECTRIC POWER CORPORATION, Seoul (KR); KOREA EAST-WEST POWER CO., LTD., Seoul (KR)

(72) Inventors: Doo-Song Gil, Daejeon (KR); Yeon-Shik Ahn, Daejeon (KR); Gye-Jo Jung, Daejeon (KR); Sang-Ki Park, Daejeon (KR)

(73) Assignees: Korea Electric Power Corporation, Seoul (KR); Korea East-West Power Co., Ltd., Seoul (KR)

( * ) Notice: Subject to any disclaimer, the term of this patent is extended or adjusted under 35 U.S.C. 154(b) by 205 days.

(21) Appl. No.: 14/427,626

(22) PCT Filed: Jul. 17, 2013

(86) PCT No.: PCT/KR2013/006388
§ 371 (c)(1),
(2) Date: Mar. 11, 2015

(87) PCT Pub. No.: WO2014/042349
PCT Pub. Date: Mar. 20, 2014

(65) Prior Publication Data
US 2015/0247823 A1    Sep. 3, 2015

(30) Foreign Application Priority Data
Sep. 14, 2012  (KR) .................. 10-2012-0102067

(51) Int. Cl.
| | | |
|---|---|---|
| *F16L 55/26* | (2006.01) | |
| *G01B 17/02* | (2006.01) | |
| *G01N 29/24* | (2006.01) | |
| *G01N 29/22* | (2006.01) | |
| *G01N 29/04* | (2006.01) | |
| *F16L 101/30* | (2006.01) | |

(52) U.S. Cl.
CPC ............ *G01N 29/043* (2013.01); *F16L 55/26* (2013.01); *G01B 17/02* (2013.01); *G01N 29/225* (2013.01);
(Continued)

(58) Field of Classification Search
CPC ............ G01N 29/043; G01N 29/2437; G01N 2291/0421; G01N 2291/0289;
(Continued)

(56) References Cited

U.S. PATENT DOCUMENTS 2,802,984 A * 8/1957 Sussman ................ G01R 29/22
324/209
3,442,349 A * 5/1969 Bosselaar ............. G01M 3/005
73/40.5 A
(Continued)

FOREIGN PATENT DOCUMENTS

CN  203023810 U  *  6/2013
CN  103411858    *  11/2016
(Continued)

*Primary Examiner* — J M Saint Surin
(74) *Attorney, Agent, or Firm* — McDermott Will & Emery LLP (57) ABSTRACT

There is provided a pipeline inspection device including: a body part contacting a pipeline and accommodating the pipeline; a coupling part coupled to the body part to enclose the pipeline; and a sensor part including a sensor on at least one of one side of the body part and one side of the coupling part which are in contact with the pipeline to inspect an internal state of the pipeline. The pipeline inspection device according to exemplary embodiments is capable of inspecting pipelines without increasing a gap between the pipelines even in a case in which the gap therebetween is relatively narrow, and is capable of readily and rapidly inspecting a large area of pipelines.

4 Claims, 6 Drawing Sheets

(52) U.S. Cl.
CPC ...... *G01N 29/2437* (2013.01); *F16L 2101/30* (2013.01); *G01N 2291/023* (2013.01); *G01N 2291/0258* (2013.01); *G01N 2291/0289* (2013.01); *G01N 2291/02854* (2013.01); *G01N 2291/0421* (2013.01); *G01N 2291/2634* (2013.01)

(58) Field of Classification Search
CPC .... G01N 2291/023; G01N 2291/02854; F16L 55/26; G01B 17/02
USPC ................................... 73/602, 596
See application file for complete search history.

(56) References Cited

U.S. PATENT DOCUMENTS 5,031,460 A * 7/1991 Kanenobu ............. G01L 9/0001
73/114.43

2009/0078049 A1* 3/2009 Sinha .................... G01N 29/02
73/623
2009/0139337 A1* 6/2009 Owens ............... G01N 29/2412
73/622
2009/0158850 A1* 6/2009 Alleyne ............... G01N 29/221
73/623
2016/0327520 A1* 11/2016 Ten Grotenhuis
........................ G01N 29/0654

FOREIGN PATENT DOCUMENTS

| GB | 2437547 | * | 10/2007 |
|----|---------|---|---------|
| JP | 2007247903 | * | 9/2007 |
| KR | 10-0668800 B1 | | 1/2007 |
| KR | 100668800 | * | 8/2007 |
| KR | 10-2008-0024570 A | | 3/2008 |
| KR | 20-2009-0003130 U | | 4/2009 |
| KR | 10-2011-0121329 A | | 11/2011 |

* cited by examiner

PIPELINE INSPECTION DEVICE AND PIPELINE INSPECTION SYSTEM

RELATED APPLICATIONS

This application is a national phase of International Application No. PCT/KR2013/006388, filed on Jul. 17, 2013, which in turn claims the benefit of Korean Application No. 10-2012-0102067, filed on Sep. 14, 2012, the disclosures of which Applications are incorporated by reference herein.

TECHNICAL FIELD

The present disclosure relates to a pipeline inspection device, and more particularly, to a pipeline inspection device and a pipeline inspection system for inspecting defects that may occur in pipelines internally and externally.

BACKGROUND ART

In the area of small-sized tube inspection, the prior art includes an eye test, a thickness measurement method, and others.

An eye test is a method of visually inspecting a physical state of a surface of an inspection object, such as corrosion, erosion, and abrasion, with the naked eye or by using an auxiliary device such as a telescope.

The eye test is advantageously used to inspect an inspection object without regard to the size of the inspection object, irrespective of a material of which the inspection object is formed, such as ferrous and nonferrous metals and magnetic materials, but cannot be used to inspect defects occurring inside pipelines.

A thickness measurement method is a method for measuring the degree of wall-thinning of a pipeline material using ultrasonic waves.

The thickness measurement method is used to measure the degree of corrosion and wall-thinning in the interior of the pipeline through measurement of the thickness of the pipeline. A measurement device is portable and convenient in terms of the use thereof and is able to detect internal defects in pipelines, but requires an excessive amount of time in a case of inspecting a large pipeline area.

In addition, pipeline inspection devices according to the related art may inspect pipelines by forcibly increasing a narrow gap between pipelines when a sensor cannot be attached to the narrow gap, and in this case, the pipelines may be deformed, causing damage to the pipelines.

DISCLOSURE

Technical Problem

An aspect of the present disclosure provides a pipeline inspection device and a pipeline inspection system capable of inspecting pipelines without increasing a gap between the pipelines even in a case in which the gap therebetween is relatively narrow.

An aspect of the present disclosure also provides a pipeline inspection device and a pipeline inspection system capable of readily and rapidly inspecting a large area of pipelines using ultrasonic guided waves.

Technical Solution

According to an aspect of the present disclosure, there is provided a pipeline inspection device including: a body part contacting a pipeline and accommodating the pipeline; a coupling part coupled to the body part to enclose the pipeline; and a sensor part including a sensor on at least one of one side of the body part and one side of the coupling part which are in contact with the pipeline to inspect an internal state of the pipeline.

The coupling part may include an opening-closing member which is partially opened to allow the pipeline to be inserted.

One end of the opening-closing member may be coupled to the body part by using a hinge so as to facilitate opening and closing operations.

The pipeline inspection device may further include a connector through which the other end of the opening-closing member is allowed to be locked to the body part or another opening-closing member.

The pipeline inspection device may further include a fixing member provided on one end of the coupling part to increase coupling force between the coupling part and the pipeline and providing tensile force to the coupling part.

The pipeline inspection device may further include an elastic body provided on one end of the coupling part to facilitate absorption of vibrations transferred to the pipeline, and displacement of the elastic body may be controlled by the fixing member.

The sensor part may include a plurality of sensors provided on the pipeline in a symmetrical manner.

The sensor may be provided as a piezoelectric sensor to inspect the interior of the pipeline using ultrasonic guided waves.

According to another aspect of the present disclosure, there is provided a pipeline inspection system including: the pipeline inspection device as described above; a processing unit processing signals collected by the pipeline inspection device to determine normality or abnormality in the interior of the pipeline; and a display unit displaying the results of the processing unit.

Advantageous Effects

A pipeline inspection device according to exemplary embodiments is capable of inspecting pipelines without increasing a gap between the pipelines even in a case in which the gap therebetween is relatively narrow.

In addition, the pipeline inspection device is capable of readily and rapidly inspecting a large area of pipelines.

DESCRIPTION OF DRAWINGS

FIG. 6($a$) is a schematic view of a longitudinal mode of ultrasonic guided waves; and FIG. 6($b$) is a graph of a waveform when ultrasonic guided waves are generated in the interior of a pipeline.

BEST MODE

Hereinafter, embodiments of the present disclosure will be described in detail with reference to the accompanying drawings.

The disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

Figure 1:
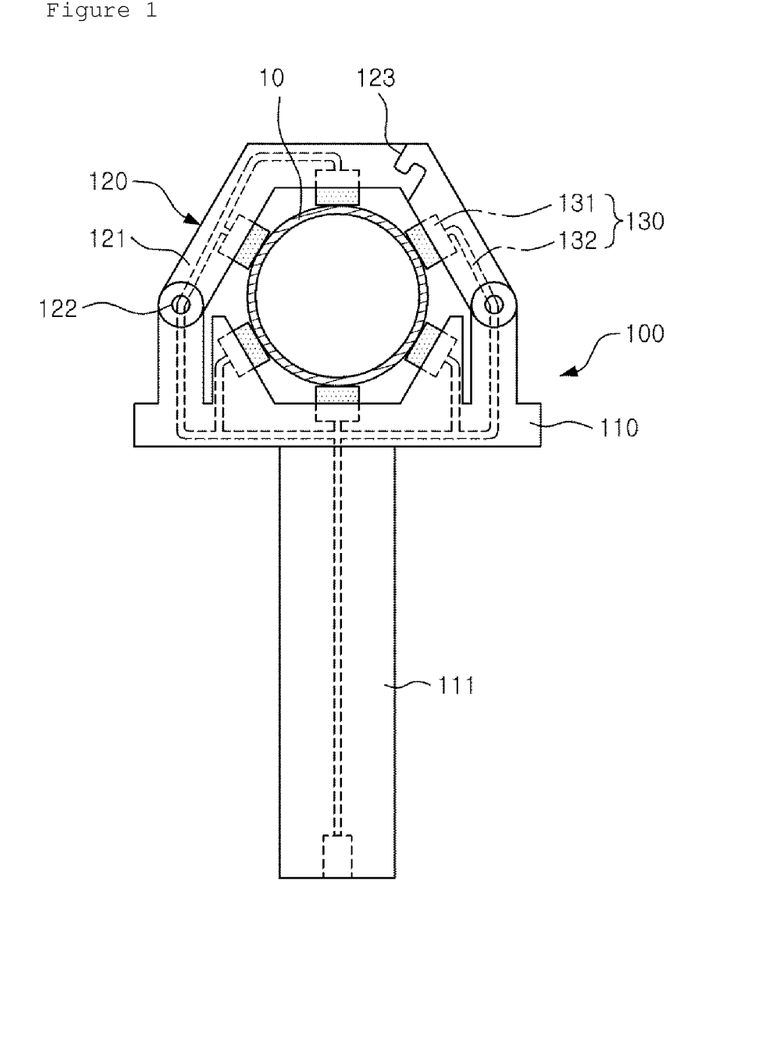
FIG. 1 is a front view of a pipeline inspection device according to an exemplary embodiment in the present disclosure.
Figure 2:
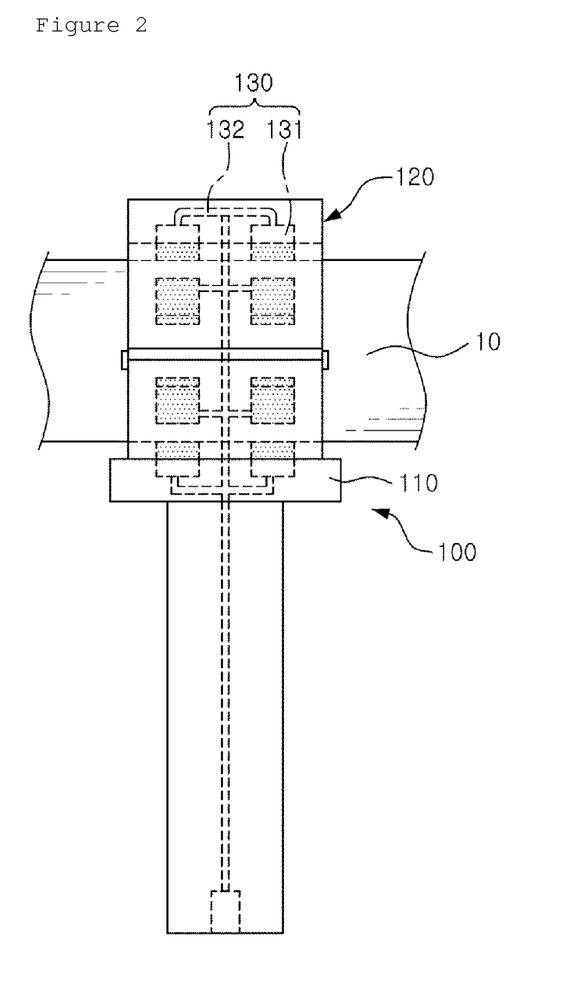
FIG. 2 is a side view of FIG. 1.

With reference to FIGS. 1 and 2, a pipeline inspection device 100 according to an exemplary embodiment in the present disclosure may include: a body part 110 accommodating a pipeline 10 to be inspected; a coupling part 120 coupled to the body part 110 to enclose the pipeline 10; and a sensor part 130 including a sensor 131 provided on the body part 110 and the coupling part 120.

One side of the body part 110 may be in contact with the pipeline 10 and accommodate the pipeline 10. When the body part 110 is positioned below the pipeline 10, the body part 110 may serve as a support supporting the pipeline 10 as well as being in contact with the pipeline 10.

In addition, a grip 111 may be provided on the other side of the body part 110 to facilitate the installation and transport of the pipeline inspection device 100 when the pipeline inspection device 100 is mounted on the pipeline 10.

The number of sensors 131 may differ according to the shape of the body part 110 in contact with the pipeline 10.

For example, as illustrated in the front view of FIG. 1, three sensors 131 may be provided to contact the body part 110 such that three surfaces of the body part 110 contact the pipeline 10.

Alternatively, in a case in which four sensors 131 are provided to contact the body part 110, four surfaces of the body part 110 may contact the pipeline 10, and various modifications thereto may be made. In addition, with reference to FIGS. 2 and 4, a plurality of sensors may be provided on a single surface in a longitudinal direction of the pipeline.

The coupling part 120 may be coupled to the body part 110 to enclose the pipeline 10. A portion of the coupling part 120 enclosing the pipeline 10 may be provided with the sensor 131 which is able to inspect an internal state of the pipeline together with the sensor 131 attached to the body part 110.

Here, the coupling part 120 may include an opening-closing member 121 which is partially opened and closed so as to insert the pipeline 10 into the interior of the coupling part 120.

In addition, a hinge 122 may be provided in a position where the body part 110 and the coupling part 120 are coupled to each other, and when the opening-closing member 121 is opened, the opening-closing member 121 may be rotated on the hinge 122 to form a space into which the pipeline 10 is to be inserted.

Preferably, the opening-closing member 121 may be significantly thin, and thus, even in a case in which a gap between the pipeline 10 and the pipeline 10 is narrow, the opening-closing member 121 may pass through the gap between the pipelines 10 such that the pipeline 10 is allowed to be inserted thereinto.

In addition, a connector 123 may be further provided in an end of the opening-closing member 121 to allow the end of the opening-closing member 121 to be locked to the body part or another opening-closing member. The connector 123 may be provided to have a "S"-like shape as illustrated in FIG. 1, thereby further increasing the coupling force of the opening-closing member 121.

Figure 3:
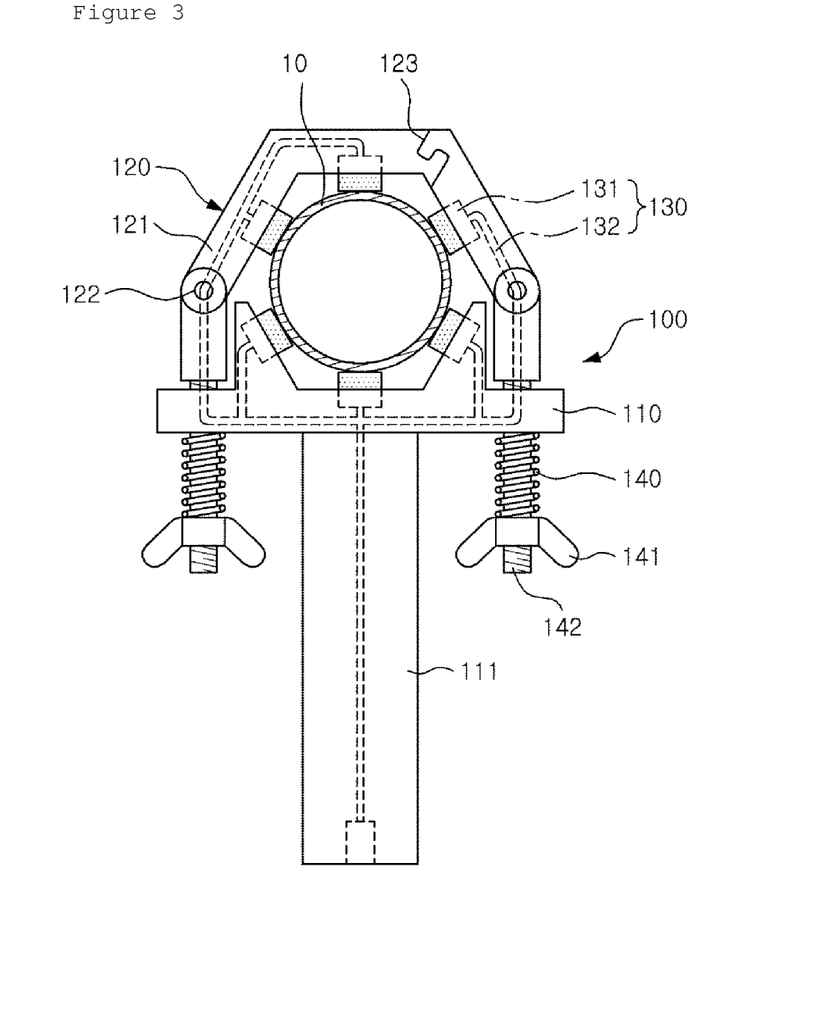
FIG. 3 is a front view of a pipeline inspection device according to another exemplary embodiment in the present disclosure.
Figure 4:
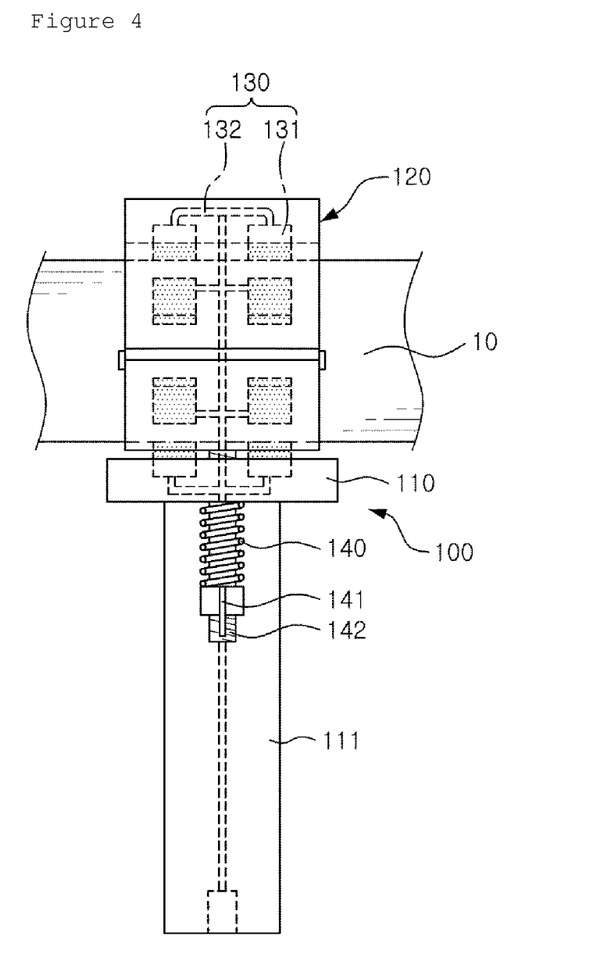
FIG. 4 is a side view of FIG. 3.

With reference to FIGS. 3 and 4, according to another exemplary embodiment, the coupling part 120 may have the opening-closing member 121 which is movable rather than being fixed to the body part 110, unlike the coupling part 120 of the pipeline inspection device illustrated in FIGS. 1 and 2.

In the pipeline inspection device illustrated in FIGS. 1 and 2, the opening-closing member 121 may be hinge-coupled to the body part 110 and may be rotated on the hinge 122, but may not be able to move in a vertical direction.

On the other hand, the pipeline inspection device 100 illustrated in FIGS. 3 and 4, according to another exemplary embodiment, may further include an extension member 142 which is extended from the opening-closing member 121 to penetrate through the body part 110 and allow the coupling part 120 to move vertically.

In addition, the extension member 142 may be hinge-coupled to the opening-closing member, and a fixing member 141 may be provided on a lower portion of the extension member 142 to fix the coupling part 120 to the body part 110.

Meanwhile, a screw thread may be formed on an outer surface of the extension member 142, and in a case in which the fixing member 141 is provided as a nut, it may be fastened to the screw thread.

However, the fixing member 141 is not limited to the nut, and may be provided as various members that are able to move the coupling part 120 vertically.

Therefore, the pipeline inspection device 100 according to this exemplary embodiment may have the opening-closing member 121 rotated on the hinge 122 and being vertically movable.

Here, when the coupling part 120 moves downwardly as the extension member 142 descends due to the movement of the fixing member 141, one side of the coupling part 120 in contact with the pipeline 10 may press the pipeline 10, and thus the coupling force between the coupling part 120 and the pipeline 10 may be increased.

On the other hand, when the coupling part 120 moves upwardly as the extension member 142 ascends due to the movement of the fixing member 141, the force generated when one side of the coupling part 120 in contact with the pipeline 10 presses the pipeline 10 may be reduced, resulting in a reduction of the coupling force.

Therefore, the coupling force of the coupling part 120 and the pipeline 10 of various diameters may be controlled by the fixing member 141 and the extension member 142.

In addition, with reference to FIGS. 3 and 4, an elastic body 140 may be further provided on one side of the extension member 142 to firmly couple the coupling part 120 to the pipeline 10.

One end of the elastic body 140 may be in contact with the body part 110, and the other end thereof may allow the coupling part 120 to closely contact the pipeline 10 by providing elastic force to the coupling part 120 during the vertical movement of the coupling part 120 while displacement thereof is controlled by the fixing member 141.

In addition, with reference to FIGS. 1 through 4, the sensors 131 may be provided on the coupling part 120 and the body part 110 to inspect the internal state of the pipeline 10, and the sensor part 130 may include the sensors 131 and a conducting wire 132 connecting the sensors 131 to each other.

In the pipeline inspection device 100 according to the exemplary embodiment, some of the plurality of sensors 131 may be attached to the body part 110 and the other sensors may be attached to the coupling part 120, such that the plurality of sensors 131 enclose the pipeline 10 and inspect normality or abnormality in the interior of the pipeline 10.

Preferably, the sensors 131 may be disposed on the outer surface of the pipeline 10 in a symmetrical manner in a circumferential direction, at least one of which may be provided in the longitudinal direction of the pipeline 10. The sensor 131 may be provided as a piezoelectric sensor so as to inspect normality or abnormality in the interior of the pipeline 10 using ultrasonic guided waves.

Hereinafter, the operational effect of the pipeline inspection device 100 according to an exemplary embodiment in the present disclosure will be detailed.

First of all, a process of coupling the pipeline inspection device 100 according to an exemplary embodiment to the pipeline 10 will be detailed.

With reference to FIGS. 1 and 2, in the pipeline inspection device 100 according to an exemplary embodiment, the opening-closing member 121 may be rotated on the hinge 122 coupling the body part 110 and the opening-closing member 121 of the coupling part 120 to open the coupling part 120.

After the opening-closing member 121 is opened and is inserted between the pipelines 10, the body part 110 may be forced to closely contact the pipeline 10 and the opening-closing member 121 may be closed to thereby couple the pipeline 10 and the coupling part 120.

Therefore, the body part 110 and the coupling part 120 of the pipeline inspection device 100 may relatively conveniently enclose the pipeline 10. In addition, in a case in which the opening-closing member 121 is significantly thin, even when the gap between the pipeline and the pipeline 10 is narrow, the opening-closing member 121 may be inserted therebetween to allow the sensor part 130 to be coupled to the pipeline 10.

In addition, the sensors 131 provided on the body part 110 and the coupling part 120 may contact the pipeline 10 while being spaced apart from each other at a predetermined distance, and may collect signals for detecting normality or abnormality in the interior of the pipeline 10 using ultrasonic waves obtained from vibrations generated by the piezoelectric elements of the sensor part 130.

Meanwhile, with reference to FIGS. 3 and 4, the pipeline inspection device 100 according to another exemplary embodiment may include the elastic body 140 and the fixing member 141 so as to allow the body part 110 and the coupling part 120 to be firmly coupled to each other, thereby allowing the sensor part 130 to closely contact the pipeline 10.

As described above, the opening-closing member 121 may be opened to allow the coupling part 120 and the body part 110 to enclose the pipeline 10. After the sensors 131 are installed on the pipeline 10, the fixing member 141 may be moved upwardly.

Then, the coupling part 120 may be moved downwardly, and the sensor part 130 provided on the coupling part 120 may more closely contact the surface of the pipeline 10.

In addition, the sensors 131 attached to the body part 110 also more closely contact the pipeline 10 as the pipeline 10 moves downwardly to apply force thereto.

In this manner, after the pipeline inspection device 100 according to the exemplary embodiment is coupled to the pipeline 10, it may transfer ultrasonic waves to the pipeline 10 by using the piezoelectric sensors and may detect normality or abnormality in the pipeline 10 using a longitudinal mode of axially symmetric modes.

Figure 6:
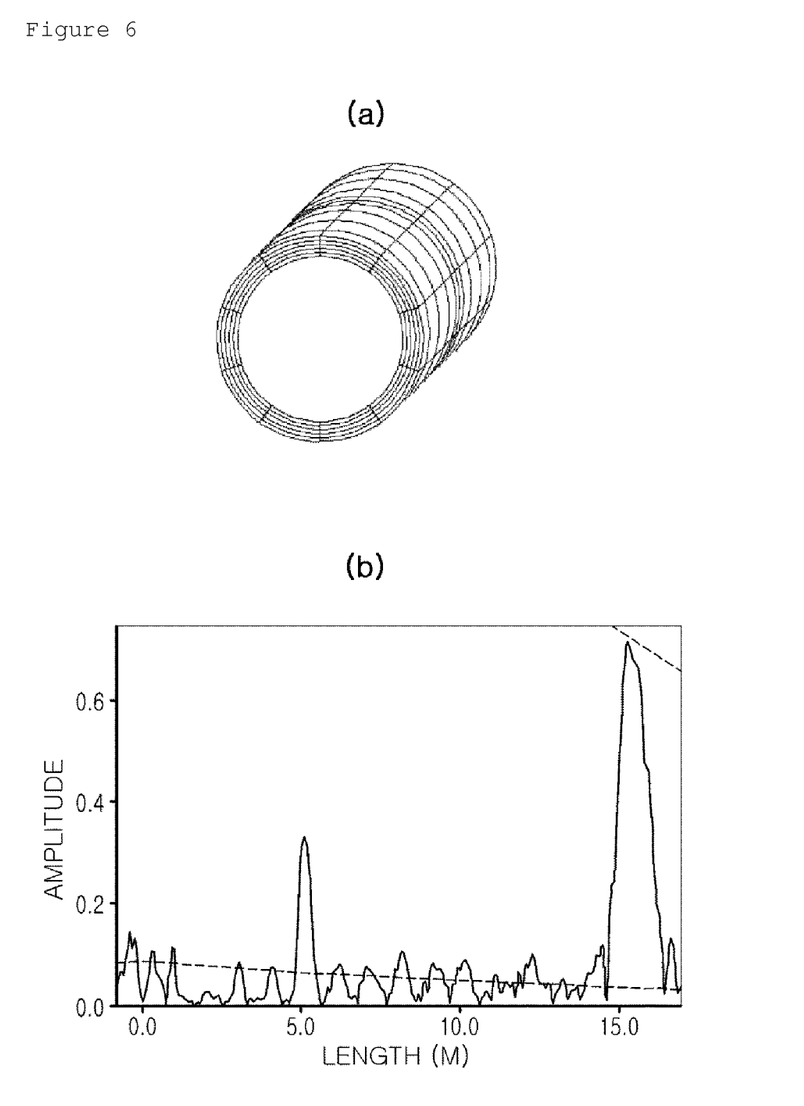

With reference to FIG. 6, the ultrasonic waves in such a longitudinal mode may only be vibrated in a longitudinal direction and a radial direction of the pipeline 10, and the generation and reception of signals may be experimentally facilitated, whereby the efficiency of the ultrasonic sensor may be improved.

With reference to FIG. 6B, if the sensor part 130 generates ultrasonic guided waves, the generated ultrasonic waves may be transferred in the longitudinal direction of the pipeline. In a case in which there is abnormality in the interior of the pipeline 10, high amplitude may appear unlike a normal waveform, and thus, the abnormality in the interior of the pipeline may be easily determined.

Figure 5:
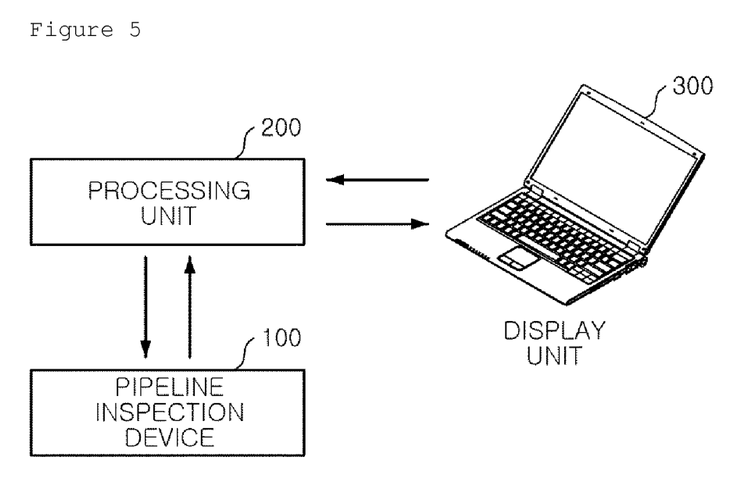
FIG. 5 is a schematic view of a pipeline inspection system according to an exemplary embodiment in the present disclosure.

That is, a pipeline inspection system according to an exemplary embodiment in the present disclosure may be able to inspect an internal state of the pipeline 10 with ease and rapidity, by coupling the pipeline inspection device 100 to the pipeline 10, analyzing a waveform of ultrasonic guided waves generated by the piezoelectric element and flowing through the interior of the pipeline 10 in a processing unit 200, and displaying normality or abnormality of the waveform at a particular point in the pipeline 10 in the form of a graph in a display unit 300.

While exemplary embodiments have been shown and described above, it will be apparent to those skilled in the art that modifications and variations could be made without departing from the scope of the invention as defined by the appended claims.

The invention claimed is:

1. A pipeline inspection device comprising:
   a body part accommodating the pipeline;
   a coupling part coupled to the body part to enclose the pipeline; and
   a sensor part including a sensor on at least one of one side of the body part and one side of the coupling part to inspect an internal state of the pipeline,
   wherein the coupling part includes:
   an opening-closing member which is partially opened to allow the pipeline to be inserted, and has a connector on one side of the opening-closing member;
   an extension member which is hinge-coupled to another side of the opening-closing member, and extends from the another side of the opening-closing member to penetrate through the body part and allow the opening-closing member to move vertically;
   a fixing member fastened to an end portion of the extension member to fix the extension member to the body part; and
   an elastic body mounted on the extension member and arranged between the body part and the fixing member.

2. The pipeline inspection device of claim 1, wherein the sensor part includes a plurality of sensors provided on the pipeline in a symmetrical manner.

3. The pipeline inspection device of claim 1, wherein the sensor is provided as a piezoelectric sensor to inspect the interior of the pipeline using ultrasonic guided waves.

4. A pipeline inspection system comprising:
   the pipeline inspection device of claim 1;
   a processing unit processing signals collected by the pipeline inspection device to determine normality or abnormality in the interior of the pipeline; and
   a display unit displaying the results of the processing unit.

* * * * *